(12) United States Patent
Bottom

(10) Patent No.: US 9,586,020 B2
(45) Date of Patent: Mar. 7, 2017

(54) MEDICAL VAPORIZER AND METHOD OF MONITORING OF A MEDICAL VAPORIZER

(71) Applicant: General Electric Company, Schenectady, NY (US)

(72) Inventor: Douglas K. Bottom, Watertown, WI (US)

(73) Assignee: General Electric Company, Schenectady, NY (US)

( * ) Notice: Subject to any disclaimer, the term of this patent is extended or adjusted under 35 U.S.C. 154(b) by 190 days.

(21) Appl. No.: 14/272,017

(22) Filed: May 7, 2014

(65) Prior Publication Data

US 2014/0238393 A1    Aug. 28, 2014

Related U.S. Application Data

(62) Division of application No. 13/052,700, filed on Mar. 21, 2011, now Pat. No. 8,752,544.

(51) Int. Cl.
*A61M 16/00* (2006.01)
*A61M 16/18* (2006.01)
(Continued)

(52) U.S. Cl.
CPC ............. *A61M 16/18* (2013.01); *G01F 1/66* (2013.01); *G01F 1/667* (2013.01); *G01F 1/74* (2013.01);
(Continued)

(58) Field of Classification Search
CPC .... A61M 16/00; A61M 16/10–16/147; A61M 16/16; A61M 16/161;
(Continued)

(56) References Cited

U.S. PATENT DOCUMENTS 2,870,764 A    1/1959    Carlson et al.
3,575,050 A *  4/1971    Lynnworth ............... G01F 1/66
                                                                    73/597
(Continued)

FOREIGN PATENT DOCUMENTS

DE    102005005349    6/2006
EP         0243515    11/1987
(Continued)

OTHER PUBLICATIONS

OSHA Directorate of Technical Support and Emergency Management, "Anesthetic Gases: Guidelines for Workplace Exposures", Jul. 20, 1999, Revised May 18, 2000, US Dept. of Labor, website address http://www.osha.gov/dts/osta/anestheticgases/index.html.
(Continued)

*Primary Examiner* — Tan-Uyen (Jackie) T Ho
*Assistant Examiner* — Ned T Heffner
(74) *Attorney, Agent, or Firm* — Andrus Intellectual Property Law, LLP

(57) ABSTRACT

The present application includes an independent and redundant measurement of anesthetic concentration, based on acoustic time-of-flight measurements, added to an anesthetic vaporizer. The redundant anesthetic concentration measurement is used to make the vaporizer inherently safe by design and monitor true vaporizer empty. Further, using an acoustic wave splitting technique and the time-of-flight measurements, the flows at the vaporizer inlet and outlet are computed. The flow measurements are used to monitor carrier gas loss, anesthetic consumption, and anesthetic delivery time remaining and provide such information to the vaporizer operator.

11 Claims, 10 Drawing Sheets

(51) Int. Cl.
*G01F 1/66* (2006.01)
*G01F 1/74* (2006.01)
*A61M 16/10* (2006.01)

(52) U.S. Cl.
CPC ... *A61M 16/104* (2013.01); *A61M 2016/1035* (2013.01); *A61M 2205/15* (2013.01); *A61M 2205/18* (2013.01); *A61M 2205/3334* (2013.01); *A61M 2205/3375* (2013.01)

(58) Field of Classification Search
CPC .............. A61M 2016/0015–2016/0042; G01N 29/00–29/036; G01F 1/66
See application file for complete search history.

(56) References Cited

U.S. PATENT DOCUMENTS

| | | | |
|---|---|---|---|
| 3,695,593 A | 10/1972 | Postlethwaite | |
| 3,943,221 A | 3/1976 | Schladitz | |
| 4,345,612 A * | 8/1982 | Koni | A61M 16/00 128/203.14 |
| 4,611,590 A | 9/1986 | Ryschka et al. | |
| 5,060,506 A | 10/1991 | Douglas | |
| 5,060,514 A | 10/1991 | Aylsworth | |
| 5,247,826 A | 9/1993 | Frola et al. | |
| 5,369,979 A | 12/1994 | Aylsworth et al. | |
| 5,536,323 A | 7/1996 | Kirlin et al. | |
| 5,546,931 A | 8/1996 | Rusz | |
| 5,581,014 A | 12/1996 | Douglas | |
| 5,644,070 A | 7/1997 | Gibboney et al. | |
| 5,645,071 A | 7/1997 | Harnoncourt et al. | |
| 5,694,924 A | 12/1997 | Cewers | |
| 5,816,242 A * | 10/1998 | Cewers | A61M 16/0051 128/200.24 |
| 5,967,141 A | 10/1999 | Heinonen | |
| 6,116,235 A | 9/2000 | Walters et al. | |
| 6,131,571 A | 10/2000 | Lampotang et al. | |
| 6,155,256 A | 12/2000 | Wallin | |
| 6,275,650 B1 | 8/2001 | Lambert | |
| 6,279,378 B1 | 8/2001 | Sheen et al. | |
| 6,488,028 B1 | 12/2002 | Lambert | |
| 6,634,864 B1 | 10/2003 | Young et al. | |
| 7,063,668 B2 | 6/2006 | Cardelius et al. | |
| 7,143,766 B2 | 12/2006 | Schuster et al. | |
| 7,415,980 B2 | 8/2008 | Hashiba | |
| 7,434,580 B2 * | 10/2008 | Downie | G01N 29/024 128/200.11 |
| 7,490,607 B2 | 2/2009 | Bottom et al. | |
| 7,886,783 B2 | 2/2011 | Rindy et al. | |
| 7,889,345 B2 | 2/2011 | Shang et al. | |
| 8,375,957 B2 | 2/2013 | Hon | |
| 2004/0093957 A1 | 5/2004 | Buess et al. | |
| 2004/0140374 A1 | 7/2004 | Snyder et al. | |
| 2004/0149285 A1 | 8/2004 | Wallen | |
| 2007/0107879 A1 | 5/2007 | Radomski et al. | |
| 2009/0090472 A1 | 4/2009 | Radomski | |
| 2009/0188490 A1 | 7/2009 | Han | |
| 2009/0255534 A1 | 10/2009 | Paterno | |
| 2010/0024616 A1 | 2/2010 | Wobben | |
| 2010/0024816 A1 | 2/2010 | Weinstein et al. | |
| 2010/0269821 A1 | 10/2010 | Larsson et al. | |
| 2012/0180724 A1 | 7/2012 | Kouketsu et al. | |

FOREIGN PATENT DOCUMENTS

| | | |
|---|---|---|
| EP | 0874238 | 10/1998 |
| EP | 0894506 | 2/1999 |
| EP | 0965372 | 12/1999 |
| EP | 1082973 | 3/2001 |
| EP | 1222940 | 7/2002 |
| EP | 0895482 | 11/2004 |
| EP | 1613383 | 10/2008 |
| EP | 2044968 | 4/2009 |
| GB | 415048 | 8/1934 |
| GB | 2029572 | 3/1980 |
| GB | 2255912 | 11/1992 |
| GB | 2279016 | 12/1994 |
| WO | 9714465 | 4/1997 |
| WO | 9736628 | 10/1997 |
| WO | 9820926 | 5/1998 |
| WO | 9844977 | 10/1998 |
| WO | 0046583 | 8/2000 |
| WO | 2004087244 | 10/2004 |
| WO | 2004091708 | 10/2004 |
| WO | 2008145177 | 12/2008 |
| WO | 2009032540 | 3/2009 |
| WO | 2011040067 | 4/2011 |

OTHER PUBLICATIONS

Search Report and Written Opinion for EP12160425.0-2204 dated Sep. 27, 2012.
Search Report and Written Opinion for EP13156712.5 dated Jun. 18, 2013.
European Search Report and Written Opinion issued in connection with related EP Application No. 13156712.5 dated Sep. 25, 2013.
Non-Final Rejection towards related U.S. Appl. No. 13/407,915 dated Apr. 23, 2014.
Final Rejection towards related U.S. Appl. No. 13/407,915 dated Nov. 17, 2014.
Final Rejection towards related U.S. Appl. No. 13/407,915 dated Apr. 6, 2015.
Non Final Rejection towards related U.S. Appl. No. 13/407,915 dated Nov. 19, 2015.

* cited by examiner

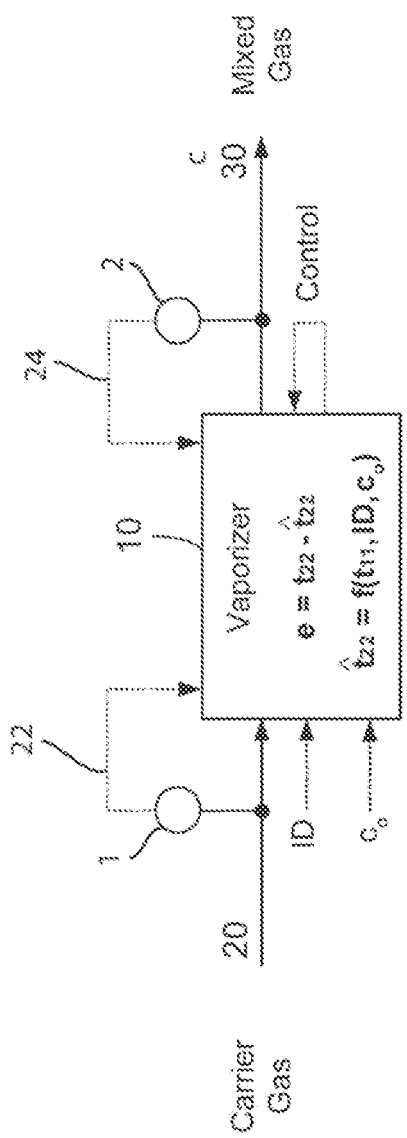
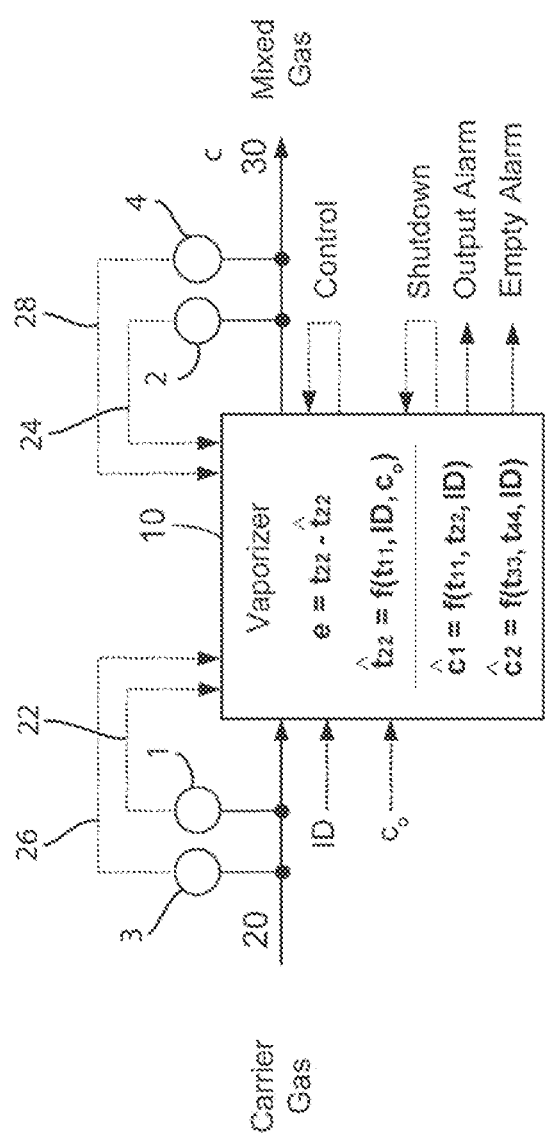

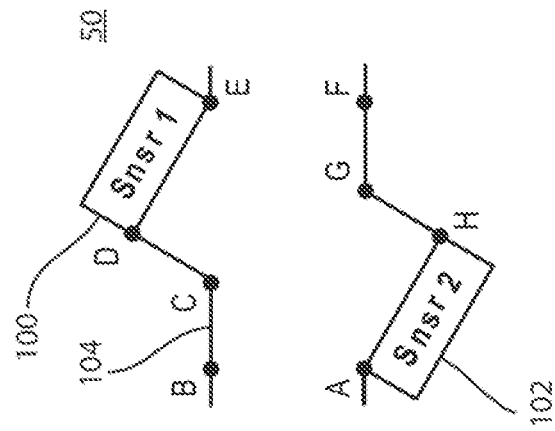
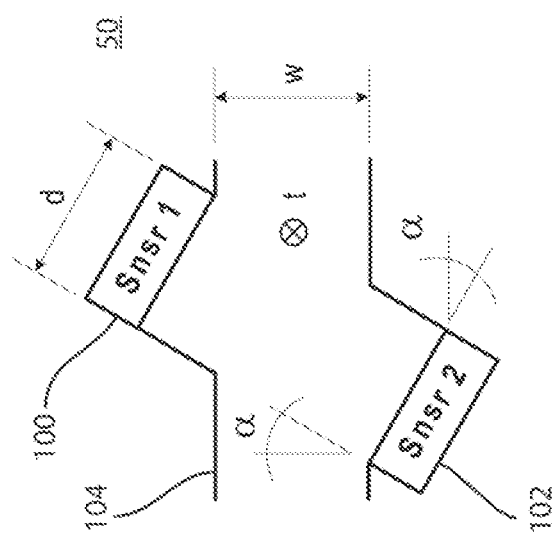
FIG. 8 (Prior Art)

FIG. 9
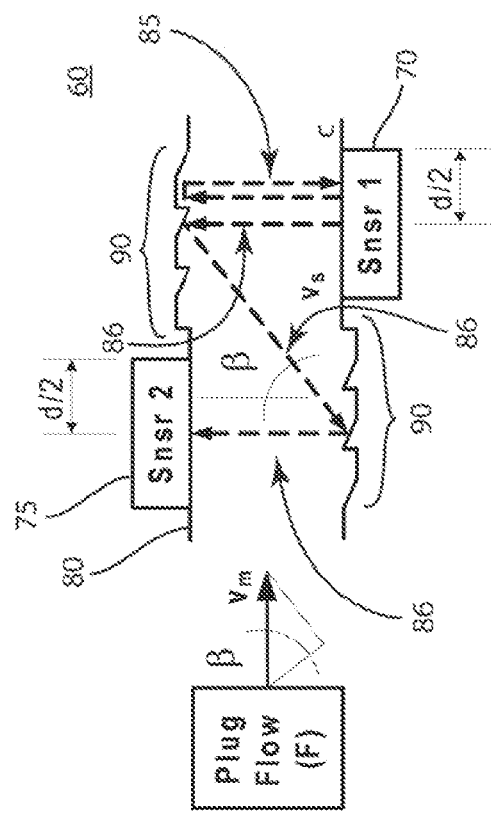
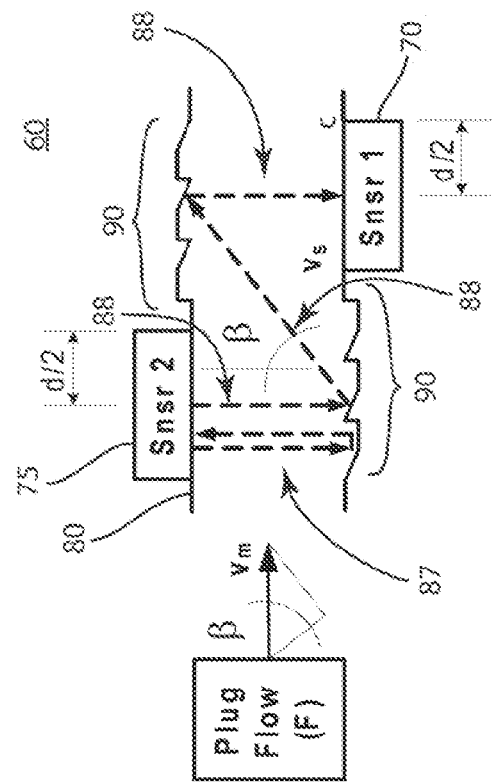

MEDICAL VAPORIZER AND METHOD OF MONITORING OF A MEDICAL VAPORIZER

CROSS-REFERENCE TO RELATED APPLICATIONS

This application is a divisional of U.S. application Ser. No. 13/052,700, filed Mar. 21, 2011, which application was published on Sep. 27, 2012, as U.S. Publication No. 2012/0240928, the content of which is incorporated herein by reference in its entirety.

FIELD

The present application is directed to both the fields of patient anesthesia systems and flow meters. More specifically, the present application is directed to the field of medical vaporizers in anesthesia systems (vaporizer) and to the field of acoustic time-of-flight flow meters used for gas composition and flow measurement (flow meter).

BACKGROUND

An anesthetic, or combination of anesthetics, may be delivered to a patient in order to produce the effects of sedation, analgesia, and neuro-muscular block, broadly referred to as anesthesia. Different anesthetics produce different effects and degrees of effects, and therefore, must be carefully delivered to the patient. When the anesthetic, or combination of anesthetics, is delivered in a gaseous form for patient inhalation, the anesthetic is combined with one or a combination of carrier gases for delivery to the patient. A vaporizer combines these two or more gases before delivery to the patient.

Acoustic wave time-of-flight (time-of-flight) t is the ratio of distance traveled (distance) D by an acoustic wave to acoustic wave speed (speed) v. As seen in FIG. 1, speed v has two components, one due to acoustic wave speed in the media (speed in media) $v_s$ in which it travels, and one due to the speed of the media itself (media speed) $v_m$, arising from flow of the media (flow) F. Speed in media $v_m$ is related to media heat capacity ratio (heat capacity ratio) γ, media temperature (temperature) T, and media molar mass (molar mass) M. Direct measurement of time-of-flight t, rather than speed v, is possible using time-of-flight sensors (sensor) 5. Practitioners will recognize that a sensor can be a fully integrated device located at the point of measurement, comprised of a transducer and other components required to acquire and report a measurement, or that a sensor can be a distributed device, minimally having a transducer located at the point of measurement, with other components located elsewhere. The inclination angle α of the sensor mounting versus the direction of flow (inclination) determines the influence of flow F on speed v. These relationships are well known to practitioners and are summarized below.

$$t = \frac{D}{v} \tag{1}$$

$$v = v_s \pm v_m \sin\alpha \tag{2}$$

$$v_s = \sqrt{\frac{\gamma RT}{M}} \tag{3}$$

t is time-of-flight
D is distance
v is speed
$v_s$ is speed in media
$v_m$ is media speed
α is inclination
γ is heat capacity ratio
R is molar gas constant
T is temperature
M is molar mass Gas composition affects speed v by modifying the speed in media $v_m$. This occurs as gas composition affects both heat capacity ratio γ and molar mass M, dependent on the amounts of the component gases present based on volumetric concentration (concentration) c. Flow F affects speed v by modifying the media speed $v_m$. These relationships are also well known to practitioners and are summarized below.

$$\gamma = 1 + \left(\frac{c}{\gamma_1 - 1} + \frac{1-c}{\gamma_2 - 1}\right)^{-1} \tag{4}$$

$$M = cM_1 + (1-c)M_2 \tag{5}$$

$$v_m = \frac{F}{A} \tag{6}$$

c is concentration of component 1
$\gamma_1$ is heat capacity ratio of component 1
$\gamma_2$ is heat capacity ratio of component 2
$M_1$ is molar mass of component 1
$M_2$ is molar mass of component 2
F is volumetric flow
A is flow cross-sectional area In general, application of the previous relationships to concentration c requires removing the effect of flow F using time-of-flight measurements t of acoustic waves traveling upstream and downstream versus flow F, then eliminating the media speed $v_m$ term using equations (1) and (2). In general, application of the previous relationships to flow F requires removing the effect of speed in media $v_s$ using time-of-flight measurements t of acoustic waves traveling upstream and downstream versus flow F, then eliminating the speed in media $v_s$ term using equations (1) and (2). These techniques are well known to practitioners and the equations involved are shown below.

$$t_u = \frac{D}{v_u} \tag{7}$$

$$v_u = v_s - v_m \sin\alpha \tag{8}$$

$$t_d = \frac{D}{v_d} \tag{9}$$

$$v_d = v_s + v_m \sin\alpha \tag{10}$$

$t_u$ is upstream time-of-flight
$v_u$ is upstream speed
$t_d$ is downstream time-of-flight
$v_d$ is downstream speed Taking anesthetic to be a first component and carrier gas to be a second component, combining equations (3)-(10) implies the general relationship below exists among the parameters at the inlet and outlet of a vaporizer. Inlet gas consists only of carrier gas. Outlet gas consists of a combination of anesthetic and carrier gas. Practitioners will recognize that the concentration c of anesthetic at the outlet of the vaporizer is synonymous with vaporizer output (output) and is the fundamental vaporizer parameter to be controlled.

$$c = f(t_{iu}, t_{id}, t_{ou}, t_{od}, \gamma_{cg}, \gamma_a, T_i, T_o, M_{cg}, M_a) \quad (11)$$

f( . . . ) denotes "is a function of", with exact form dependent on context
c is output
$t_{iu}$ is inlet upstream time-of-flight
$t_{id}$ is inlet downstream time-of-flight
$t_{ou}$ is outlet upstream time-of-flight
$t_{od}$ is outlet downstream time-of-flight
$\gamma_{cg}$ is carrier gas heat capacity ratio
$\gamma_a$ is anesthetic heat capacity ratio
$T_i$ is inlet temperature
$T_o$ is outlet temperature
$M_{cg}$ is carrier gas molar mass
$M_a$ is anesthetic molar mass Referring back to earlier discussion, combining equations (6)-(10) and converting volumetric flow to volumetric flow at standard conditions using the Ideal Gas Law, implies the general relationships below exist.

$$F_i = f(t_{iu}, t_{id}, P_i, P, T_i, T) \quad (12)$$

$$F_o = f(t_{ou}, t_{od}, P_o, P, T_o, T) \quad (13)$$

$F_i$ is inlet flow at standard conditions
$P_i$ is inlet pressure
P is standard pressure
$T_i$ is inlet temperature
T is standard temperature
$F_o$ is outlet flow at standard conditions
$P_o$ is outlet pressure
$T_o$ is outlet temperature U.S. patent application Ser. No. 12/648,602 describes a scheme (prior vaporizer) to control output c from a vaporizer using a negative feedback controller based on time-of-flight measurements $t_i$, $t_o$ at the inlet and outlet of the vaporizer as suggested by equation (11). This involves computing a target outlet time-of-flight $\hat{t}_o$ from the inlet time-of-flight $t_i$, the anesthetic identity ID, and the commanded output $c_o$. Then, an error signal e is formed for the outlet time-of-flight $t_o$. Finally, an actuator throttling the amount of anesthetic delivered from the vaporizer is driven from the error signal e to control output. Judicious mounting of sensors at the vaporizer inlet and outlet to negate the effect of flow F on speed v, maintaining the inlet and outlet at similar temperatures T to negate the effect of temperature variation, and the use of singular nominal values for heat capacity ratio γ and molar mass M for all possible combinations of carrier gas to make the vaporizer independent of the carrier gas source enable a simpler, less costly, and more available vaporizer than suggested by equation (11). The prior vaporizer was reported applicable to controlling a wide range of anesthetics, including, but not limited to, Desflurane, Enflurane, Halothane, Isoflurane, Sevoflurane, and Xenon in a wide range of carrier gases, including, but not limited to, air, carbon dioxide, heliox, nitrous oxide, and oxygen.

Risk management regulations require control measures be provided in a vaporizer to make it safe for patient use, with an inherently safe design being optimum. An inherently safe vaporizer design operates in such a way that it self detects unsafe conditions and shuts down anesthetic output without operator setup, monitoring, or intervention. The primary patient hazards associated with vaporizer use are over and under delivery of anesthetic. It is an objective of the present application to create a method whereby the prior vaporizer is extended to be an inherently safe design with respect to over and under delivery of anesthetic. A secondary patient hazard associated with vaporizer use is loss of carrier gas. It is an objective of the present application to create a method whereby the prior vaporizer is extended to monitor carrier gas loss within the vaporizer.

For a vaporizer operator (operator), two beneficial quantities to know are (1) anesthetic consumption (consumption) during a time period for patient billing purposes, and (2) anesthetic delivery time remaining (time remaining) at the current output and carrier gas flow input for vaporizer refilling purposes. The present application includes a method whereby the prior vaporizer is extended to monitor consumption. The present application also includes a method whereby the prior vaporizer is extended to monitor time remaining.

Application of time-of-flight t to flow F requires an implementation where flow F affects speed v. In the prior art, this is typically accomplished using a physical configuration where the sensors 5 are positioned with an inclination a to the direction of flow F, as seen in FIG. 1. In this manner, media speed $v_m$ has a component along the direction of acoustic wave 7 travel. Flow meter design, however, is a tradeoff of several design parameters that affect implementation feasibility, performance, and cost.

Three significant design parameters of time-of-flight flow meters used for gas composition and flow are (1) time-of-flight magnitude, (2) time-of-flight change magnitude, and (3) flow meter volume. The former two parameters must be reconciled with commercially available sensors and electronics, with maximization of both time-of-flight magnitude and time-of-flight change magnitude being preferred. The latter parameter of the three determines the speed of flow meter response to composition changes, as media in the flow meter must be fully exchanged for proper detection, with minimization of flow meter volume being preferred. The present application includes a new flow meter configuration whereby the tradeoff between the time-of-flight change magnitude and flow meter volume is improved versus the prior art.

SUMMARY

A system for the delivery of anesthetics includes a breathing circuit configured to deliver a combined gas to a patient, sourcing the combined gas as follows. An inlet conduit for carrier gas conveys a flow of carrier gas from a carrier gas source to a vaporizer. A conduit for anesthetic conveys a flow of anesthetic from an anesthetic source. An actuator throttles the flow of anesthetic from the anesthetic source to enable control of the amount of anesthetic taken from the anesthetic source. The vaporizer mixes the carrier gas and anesthetic flows into a combined gas. A controller receives a command indicating the desired amount of anesthetic in the combined gas and operates the actuator to achieve the desired amount. An outlet conduit conveys the combined gas from the vaporizer to a breathing circuit.

The present application is an improvement upon the vaporizer described in U.S. patent application Ser. No. 12/648,602, the prior vaporizer having an inlet conduit for carrier gas, an anesthetic source, an actuator able to throttle the amount of anesthetic mixed into the carrier gas, an outlet conduit for combined carrier gas and anesthetic, a first sensor disposed along the inlet conduit, a second sensor disposed along the outlet conduit, a negative feedback controller, and an input for commanded output. The controller is able to drive the actuator, and it receives a first sensor signal and a second sensor signal from the first and second sensors respectively.

In the prior vaporizer, the method of controlling output included establishing a target anesthetic concentration from the commanded output. The first sensor measures time-of-flight through the carrier gas and the second sensor measures time-of-flight through combined anesthetic and carrier gas. The controller computes a target time-of-flight for the combined anesthetic and carrier gas and compares the target time-of-flight for the second sensor and the time-of-flight from the second sensor. The controller drives the actuator to adjust the amount of anesthetic in the combined anesthetic and carrier gas.

In the present application, third and fourth sensors, disposed along the inlet and outlet conduits respectively, are added, along with signal transmission from both sensors to the controller. The signals from all four sensors, along with added functionality in the controller, are used to extend the prior vaporizer to be inherently safe by design and enhanced with useful monitoring functions for the operator.

Independent monitoring of output and detection of true empty are provided using the signals from all four sensors and additional controller functionality. The controller computes output independently using signals from the first and second, and third and fourth, sensor pairs respectively. The controller compares output computations. If the difference exceeds a limit, the controller shuts down the vaporizer and provides an output alarm. If the difference is below a limit, the commanded output is nonzero, and computed output is below a limit, the controller provides an empty alarm.

Carrier gas loss monitoring is provided using the signals from all four sensors and additional controller functionality. The controller computes the flow at the inlet and outlet conduits using signals from the first and third, and second and fourth, sensor pairs respectively. The controller computes the carrier gas loss from the computed flows at the inlet and outlet conduits, taking into account flow due to anesthetic. If the computed carrier gas loss exceeds a limit, the controller shuts down the vaporizer and provides a leak alarm.

Consumption monitoring is provided using the signals from all four sensors and additional controller functionality. The controller computes output using signals from the first and third sensors. The controller computes the flow at the outlet conduit using signals from the second and fourth sensors. The controller computes the consumption rate from the computed flow at the outlet conduit and the computed output. The controller computes consumption by integrating the consumption rate over a period of time and provides consumption information.

If anesthetic level remaining information (level) is available to the vaporizer, time remaining is provided using the signals from all four sensors and additional controller functionality. The controller computes output using signals from the first and third sensors. The controller computes the flow at the outlet conduit using signals from the second and fourth sensors. The controller computes the consumption rate from the computed flow at the outlet conduit and the computed output. The controller computes the time remaining by dividing the consumption rate into the level and provides time remaining information.

In the present application, a flow meter has a conduit for media flow. A first sensor and a second sensor, both able to measure time-of-flight, are both mounted to the conduit without inclination to the direction of flow. The first sensor and the second sensor, generate a first a signal and a second signal, respectively indicative of time-of-flight. The conduit has wall surfaces with both flat and angled areas with which acoustic waves from both sensors may interact.

The first sensor and the second sensor, transmit an acoustic wave to, and receive an acoustic wave from, themselves individually (pulse-echo mode) by interacting with the flat areas. The first sensor and the second sensor, transmit an acoustic wave to, the second sensor and the first sensor, respectively pair-wise (transmit-receive mode) by interacting with the angled areas.

The flow meter provides the time-of-flight signals obtained in pulse-echo mode for use in gas-composition-related computations. The flow meter provides the time-of-flight signals obtained in transmit-receive mode for use in flow-related computations. Conduit volume is reduced for a given time-of-flight change magnitude, or time-of-flight change magnitude is increased for a given conduit volume for the flow meter in the present application versus that in the prior art,

BRIEF DESCRIPTION OF THE FIGURES

FIG. 2 depicts a prior vaporizer for controlling anesthetic output of the prior art.

FIG. 3 depicts an embodiment of the vaporizer of the present application, extending the prior vaporizer to independently monitor anesthetic output.

FIG. 8 depicts the construction of a prior art acoustic time-of-flight flow meter for gas composition and flow.

FIG. 9 depicts an embodiment of acoustic wave flight paths in an acoustic time-of-flight flow meter according to the present application.

DETAILED DESCRIPTION

Figure 11:
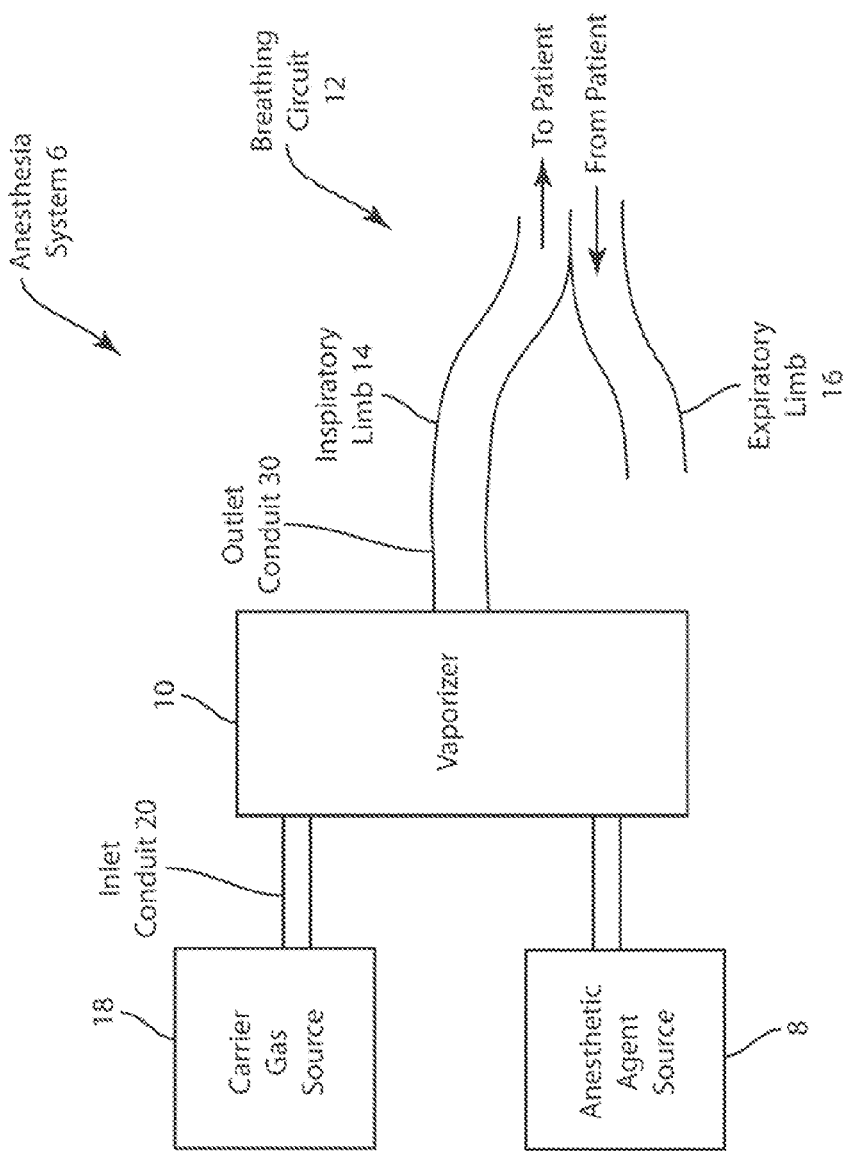
FIG. 11 depicts an embodiment of an anesthesia system according to the present application.

An exemplary anesthesia system 6 utilizing a vaporizer 10 is depicted in FIG. 11. The anesthesia delivery system 6 includes a breathing circuit 12 with an inspiratory limb 14 and an expiratory limb 16. The inspiratory limb 14 delivers a combined gas, as will be described in further detail herein, to a patient. While in some systems the patient is permitted to exhale into the ambient room atmosphere, requiring no expiration limb 16, often the patient exhalation is directed through the expiratory limb 16. The expiratory limb 16 of the breathing circuit 12 directs the expired breath from the patient to treatment devices (not depicted) such as, but not limited to, anesthetic scavenging devices or carbon dioxide absorbers that treat the expired breath before releasing the gas into the room or recirculating the excess anesthetic and/or other exhaled gases back to the patient through the breathing circuit 12.

The anesthesia system 6 further includes a carrier gas source 18 and an anesthetic source 8. The carrier gas source 18 may include a source or sources of one or more of a variety of gases to be delivered to the patient. These gases may include, but are not limited to, air, carbon dioxide, heliox, nitrous oxide, and oxygen. Each of these carrier gases, alone or in combination with other gases, provide ventilatory benefits to the patient, as well as provide a transport gas for the delivery of the anesthetic. The combination of the carrier gas with the anesthetic not only provides the patient with the respiratory benefits derived from the carrier gas and anesthesia treatment, but also provides a setting wherein the amount of the anesthetic may be controlled as a percentage of the resulting combined gas, when the anesthetic is mixed with the carrier gas and provided to the patient.

The anesthetic source 8 may contain any of a variety of anesthetics, such as, but not limited to, Desflurane, Enflurane, Halothane, Isoflurane, Sevoflurane, and Xenon. These are often provided one at a time, as particular combinations of anesthetics may degrade and produce undesirable by-products. However, the anesthetic source 8 may include a plurality of anesthetics, which are delivered in a succession to provide more sophisticated anesthesia of the patient using the properties of a plurality of anesthetics.

A supply of carrier gas from the carrier gas source 18 is conveyed by an inlet conduit 20 to the vaporizer 10. A supply of anesthetic is provided from the anesthetic source 8 to the vaporizer 10. The carrier gas and the anesthetic supplied to the vaporizer 10 are mixed in the vaporizer 10 such that the anesthetic is transported along with the carrier gas in a combined gas. The combined gas from the vaporizer 10 is conveyed by an outlet conduit 30 to the inspiratory limb 14 and thus to the breathing circuit 12. A controller (not depicted) receives a command from the anesthesia system 6 indicating the desired amount of anesthetic in the combined gas and operates an actuator (not depicted), able to throttle the amount of anesthetic from the anesthetic source 8, to achieve the desired amount. In this manner, the amount of anesthetic in the resulting combined gas is controlled for delivery to the patient.

The controller (not depicted) may be physically configured in the vaporizer 10, or configured outside the vaporizer 10, in the anesthesia system 6. The controller (not depicted) is in communication with sensors to receive their signals and with the actuator via a control signal to operate it. The controller (not depicted), which includes a processor and storage medium, is configured to receive all signals required for computations and make such computations.

U.S. patent application Ser. No. 12/648,602 describes a vaporizer to control output c from a vaporizer using time-of-flight measurements t from sensors as summarily depicted in FIG. 2, based on the control equations listed below and the configuration that follows.

$$e = t_{22} - \hat{t}_{22} \quad (14)$$

$$\hat{t}_{22} = f(t_{11}, ID, c_o) \quad (15)$$

e is error signal
$t_{XY}$ is time-of-flight from sensor X to Y
$\hat{}$ is computed and/or target value
$c_o$ is commanded output A first sensor 1, disposed along the inlet conduit 20 of the vaporizer 10, generates a first time-of-flight signal (signal) 22 indicative of the time $t_{11}$ required for an acoustic wave to pass across the inlet conduit 20, that conveys inlet flow $F_i$ into the vaporizer 10. A second sensor 2, disposed along the outlet conduit 30 of the vaporizer 10, generates a second time-of-flight signal 24 indicative of the time $t_{22}$ required for an acoustic wave to pass across the outlet conduit 30, that conveys outlet flow $F_o$ from the vaporizer 10. A controller (not depicted) computes a target second time-of-flight $\hat{t}_{22}$ based on a first time-of-flight $t_{11}$, anesthetic identity ID, and commanded output $c_o$ from the operator. An error signal e is formed for the second time-of-flight $t_{22}$, and the controller (not depicted) manipulates a control signal (Control) based on a negative feedback scheme (not depicted) in order to operate an actuator (not depicted) throttling the anesthetic source (not depicted) within the vaporizer 10. In this manner, the output c from the vaporizer 10 can be controlled to match the commanded output $c_o$ from the operator. In an embodiment, the sensors 1, 2 are ultrasonic time-of-flight sensors.

FIGS. 3-6 depict a vaporizer 10, as configured in the prior vaporizer, now with an expanded configuration for monitoring output c, carrier gas loss, consumption, and delivery time remaining according to the present application. A third sensor 3, positioned upstream of the first sensor 1 and disposed along the inlet conduit 20 of the vaporizer 10, generates a third signal 26 indicative of the time t required for an acoustic wave to pass across the inlet conduit 20. A fourth sensor 4, positioned downstream of the second sensor 2 and disposed along the outlet conduit 30 of the vaporizer 10, generates a fourth signal 28 indicative of the time t required for an acoustic wave to pass across the outlet conduit 30. In an embodiment, the sensors 1, 2, 3, 4 are ultrasonic time-of-flight sensors. Further, the controller (not depicted) is enhanced with additional functionality to implement the expanded configuration of the present application as discussed in detail below.

In one embodiment of the present application, implementation details enable a simpler, less costly, and more available vaporizer 10. A novel construction of both the inlet conduit 20 and outlet conduit 30 is employed such that acoustic waves may travel in separate paths from each individual sensor 1, 2, 3, 4, one unaffected by flows $F_i$, $F_o$ useful for monitoring gas concentration c, and the other affected by flows $F_i$, $F_o$, useful for monitoring flows $F_i$, $F_o$. The inlet conduit 20 and outlet conduit 30 are maintained at approximately the same temperature T. The range of possible heat capacity γ and molar mass M values for all carrier gases are reduced to singular nominal values, one for carrier gas heat capacity and one for carrier gas molar mass. After incorporating these changes, the relationship in equation (11) can be simplified as shown below, with the nominal values buried in the function "f( . . . )".

$$c = f(t_i, t_o, \gamma_a, M_a) \quad (16)$$

$t_i$ is inlet time-of-flight in path unaffected by flow
$t_o$ is outlet time-of-flight in path unaffected by flow
In this manner, computing output ĉ is made simpler and more accurate, requiring only two time-of-flight measurements $t_i$, $t_o$ and not being subject to error introduced from removing the effect of flows $F_i$, $F_o$. In this manner, computing output ĉ is also made less costly to the manufacturer of vaporizer 10 and more available to the operator of vaporizer 10, not requiring additional sensing or communication hardware, nor being subject to the accompanying failures, of temperature sensors or an information link to the carrier gas source from the vaporizer 10.

FIG. 3 depicts a vaporizer 10 configured for output c control, now expanded for monitoring output c according to the present application. The controller (not depicted) makes a first output computation $\hat{c}_1$ of output c at the outlet conduit 30 from the time-of-flight $t_{11}$ indicated by the first signal 22, the time-of-flight $t_{22}$ indicated by the second signal 24, and anesthetic identity ID, as shown below. The controller (not depicted) makes a second output computation $\hat{c}_2$ of output c at the outlet conduit 30 from the time-of-flight $t_{33}$ indicated by the third signal 26, the time-of-flight $t_{44}$ indicated by the fourth signal 28, and anesthetic identity ID, independent of the first output computation $\hat{c}_1$, as shown below. Knowledge of anesthetic identity ID is required to select the proper heat capacity $\gamma_a$ and molar mass $M_a$ values for the anesthetic as well as the exact form for the function "f( . . . )" in the computations.

$$\hat{c}_1 = f(t_{11}, t_{22}, ID) \tag{17}$$

$$\hat{c}_2 = f(t_{33}, t_{44}, ID) \tag{18}$$

ID is anesthetic identity
$\hat{c}_1$ is first output computation
$\hat{c}_2$ is second output computation The controller (not depicted) computes the difference between the first output computation $\hat{c}_1$ and the second output computation $\hat{c}_2$ and compares the difference to a limit. If the difference exceeds the limit, the controller (not depicted) provides a shutdown signal (Shutdown) which causes the vaporizer 10 to halt delivery of anesthetic, and provides an output alarm signal (Output Alarm). In a properly functioning vaporizer 10, the independent first output computation $\hat{c}_1$ and second output computation $\hat{c}_2$ should agree within tolerances. Thus, the proposed vaporizer according to the present application extends the prior vaporizer to be inherently safe with regards to over and under delivery of anesthetic.

The previous discussion, as well as the discussion below, includes comparing computations to limits. The manufacturer of the vaporizer and/or system predetermines these limits analytically and/or empirically. Where patient safety is involved, these limits reflect safety levels as required by applicable standards for the patient being monitored and/or treated. Where patient safety is not involved, these limits reflect useful and commercially competitive levels of vaporizer performance.

In addition to monitoring output c, the vaporizer configuration depicted in FIG. 3 can be used to detect true vaporizer empty. The controller (not depicted) makes two independent computations of output $\hat{c}_1$, $\hat{c}_2$ using equations (17) and (18), computes the difference between the output computations $\hat{c}_1$, $\hat{c}_2$, and compares the difference to a limit, all in the manner as previously described for monitoring output c. If the difference is below the limit, the controller (not depicted) computes the difference between the first output computation $\hat{c}_1$ and the commanded output $c_o$ and compares the difference to a limit. If the difference exceeds the limit, the controller (not depicted) provides an empty alarm signal (Empty Alarm). In a properly functioning vaporizer 10 with anesthetic remaining, the first output computation $\hat{c}_1$ and second output computation $\hat{c}_2$ should agree within tolerances, and the first output computation $\hat{c}_1$ and commanded output $c_o$ should agree within tolerances. Thus, the proposed vaporizer according to the present application extends the prior vaporizer to detect true empty, a condition where no anesthetic is available, a point beyond where there is anesthetic remaining but below detection by a level sensor, or even further where there is not even any residual anesthetic remaining in wicking material.

In one embodiment of the present application, implementation details enable a simpler and less costly vaporizer 10. The inlet conduit 20 and outlet conduit 30 are maintained at approximately the same temperature T. The range of possible inlet temperature $T_i$ and outlet temperature $T_o$ values is reduced to a singular nominal value. The range of possible inlet pressure $P_i$ and outlet pressure $P_o$ values is reduced to a singular nominal value. After incorporating these changes, the relationships in equations (12) and (13) are as shown below, with the nominal and standard values buried in the function "f( . . . )".

$$F_i = f(t_{iu}, t_{id}) \tag{19}$$

$$F_o = f(t_{ou}, t_{od}) \tag{20}$$

In this manner, computing flows $F_i$, $F_o$ is made simpler, requiring only two time-of-flight measurements $t_{iu}$, $t_{id}$ and $t_{ou}$, $t_{od}$ each for inlet flow $F_i$ and outlet flow $F_o$ to be calculated. In this manner, computing flows $F_i$, $F_o$ is also made less costly to the manufacturer of vaporizer 10 and more available to the operator of vaporizer 10, not requiring additional sensing hardware, nor being subject to the accompanying failures, of pressure sensors or temperature sensors.

Figure 1:
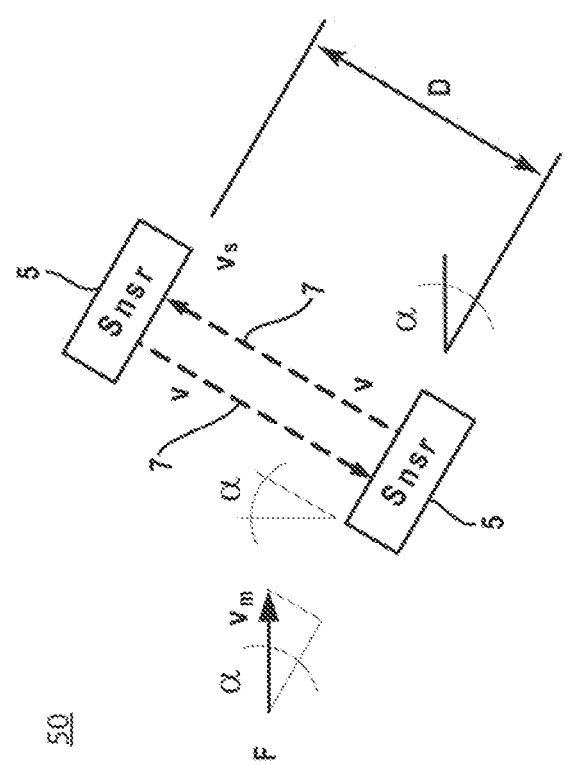
FIG. 1 depicts the general behavior of acoustic wave flight in the presence of media flow.
Figure 4:
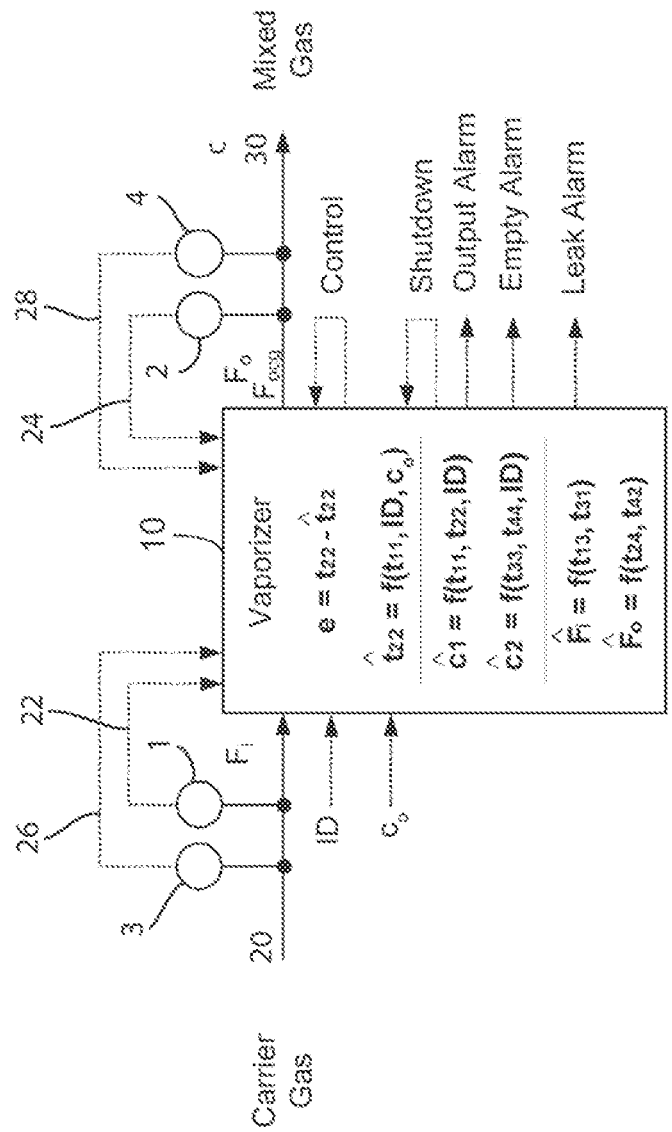
FIG. 4 depicts a further embodiment of the vaporizer of the present application that monitors carrier gas loss.

FIG. 4 depicts a vaporizer 10 configured for output c control and expanded for monitoring output c as previously described according to the present application, now further expanded for monitoring carrier gas loss according to the present application. The controller (not depicted) computes output $\hat{c}$ at the outlet conduit 30 using equation (17), as previously described for monitoring output c. The controller (not depicted) computes inlet flow $\hat{F}_i$ from the time-of-flight $t_{31}$ indicated by the first signal 22 and the time-of-flight $t_{13}$ indicated by the third signal 26, as shown below. The controller (not depicted) computes outlet flow $\hat{F}_o$ from the time-of-flight $t_{42}$ indicated by the second signal 24 and the time-of-flight $t_{24}$ indicated by the fourth signal 28, as shown below. The controller (not depicted) computes outlet carrier gas flow $\hat{F}_{ocg}$ at the outlet conduit 30 from computed outlet flow $\hat{F}_o$ and the first computed output $\hat{c}_1$, as shown below, accounting for the presence of anesthetic using the definition of anesthetic concentration on a volumetric basis.

$$\hat{F}_i = f(t_{13}, t_{31}) \tag{21}$$

$$\hat{F}_o = f(t_{42}, t_{24}) \tag{22}$$

$$\hat{F}_{ocg} = f(\hat{F}_o, \hat{c}_1) \tag{23}$$

$\hat{F}_i$ is inlet flow computation
$\hat{F}_o$ is outlet flow computation
$\hat{F}_{ocg}$ is outlet carrier gas flow computation The controller (not depicted) computes the difference between the inlet flow computation $\hat{F}_i$ and the outlet carrier gas outlet flow computation $\hat{F}_{ocg}$ and compares the difference to a limit. If the difference exceeds the limit, the controller (not depicted) provides a leak alarm signal (Leak Alarm). In a properly functioning vaporizer 10, the flow of carrier gas as computed at the inlet conduit 20, being the inlet flow computation $\hat{F}_i$, and the flow of carrier gas as computed at the outlet conduit 30, being the outlet carrier gas flow computation $\hat{F}_{ocg}$, should agree within tolerances.

Thus, the proposed vaporizer according to the present application extends the prior vaporizer to monitor carrier gas loss within the vaporizer 10.

Figure 5:
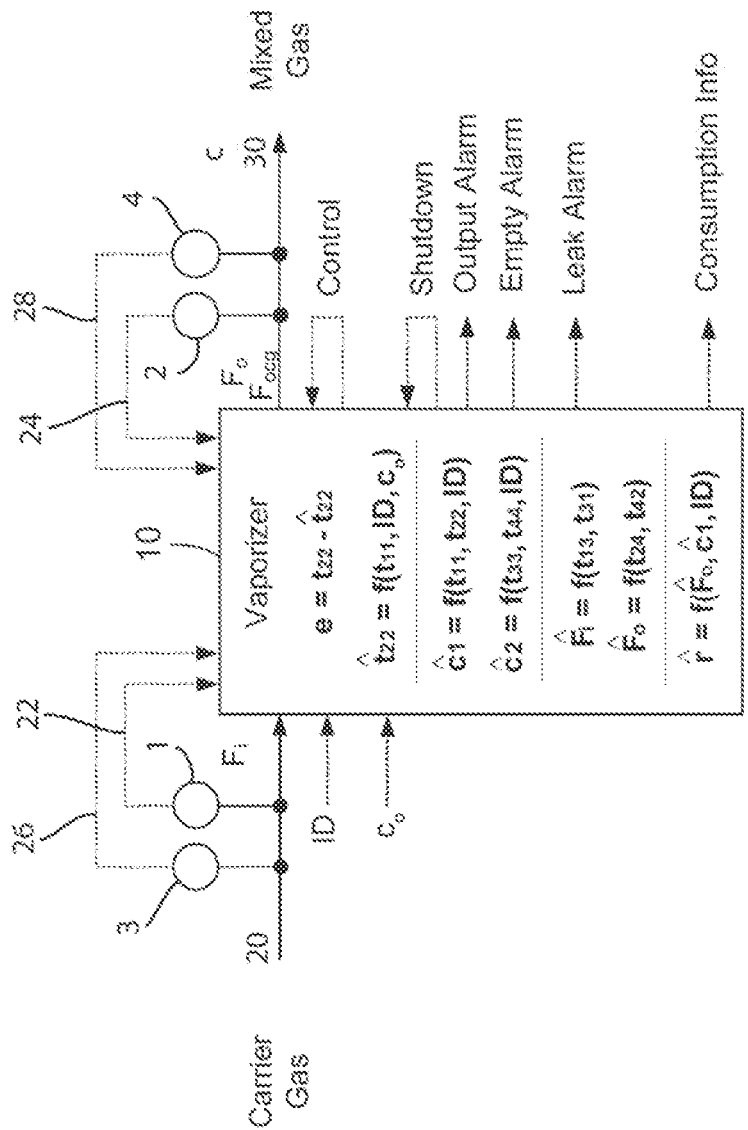
FIG. 5 depicts a further embodiment of the vaporizer of the present application that monitors anesthetic consumption.

FIG. 5 depicts a vaporizer 10 configured for output c control, expanded for monitoring output c and carrier gas loss (Leak Alarm) as previously described according to the present application, now further expanded for monitoring consumption according to the present application. The controller (not depicted) computes output ĉ at the outlet conduit 30, using equation (17), as previously described for monitoring output c. The controller (not depicted) computes outlet flow $\hat{F}_o$, using equation (22), as previously described for monitoring carrier gas loss. The controller (not depicted) computes consumption rate $\hat{r}$ as shown below, utilizing computed outlet flow $\hat{F}_o$, computed first output $\hat{c}_1$, anesthetic identity ID, and if the anesthetic is stored in liquid form, published anesthetic liquid density or specific gravity data.

$$\hat{r} = f(\hat{F}_o, \hat{c}_1, ID) \quad (24)$$

$\hat{r}$ is consumption rate computation

The controller (not depicted) integrates the computed consumption rate $\hat{r}$ during a time period to compute consumption and provides consumption information (Consumption Info). Thus, the proposed vaporizer according to the present application extends the prior vaporizer to monitor consumption.

Figure 6:
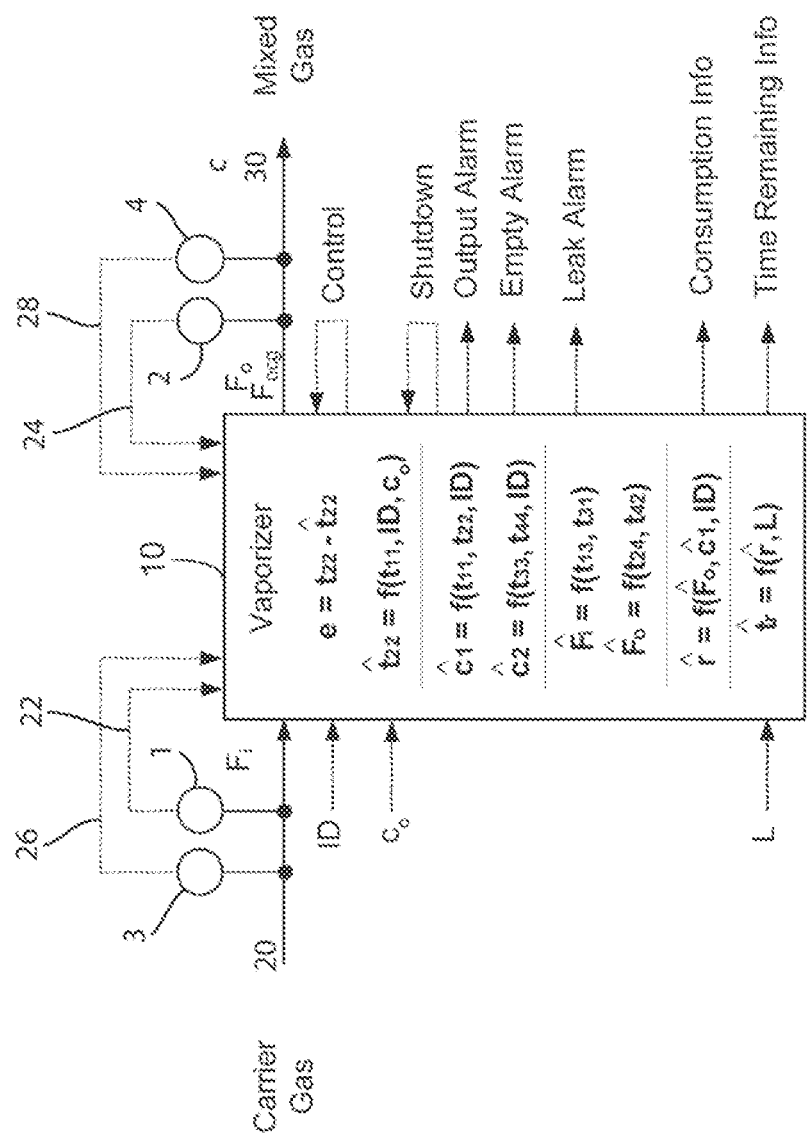
FIG. 6 depicts a further embodiment of the vaporizer of the present application that monitors anesthetic delivery time remaining.

FIG. 6 depicts a vaporizer 10 configured for output c control, expanded for monitoring output c, carrier gas loss (Leak Alarm), and consumption (Consumption Info) as previously described according to the present application, now further expanded for monitoring time remaining according to the present application. The controller (not depicted) computes consumption rate $\hat{r}$ using equation (24), as previously described for monitoring consumption. The controller (not depicted) computes time remaining $\hat{t}_r$ as shown below, provided level L is available as an input.

$$\hat{t}_r = f(\hat{r}, L) \quad (25)$$

$\hat{t}_r$ is time remaining computation
L is level

The controller (not depicted) divides the computed consumption rate $\hat{r}$ into level L to compute time remaining $\hat{t}_r$ and provides time remaining information (Time Remaining Info). Thus, if level L is available as an input, the proposed vaporizer according to the present application extends the prior vaporizer to monitor time remaining.

Figure 7:
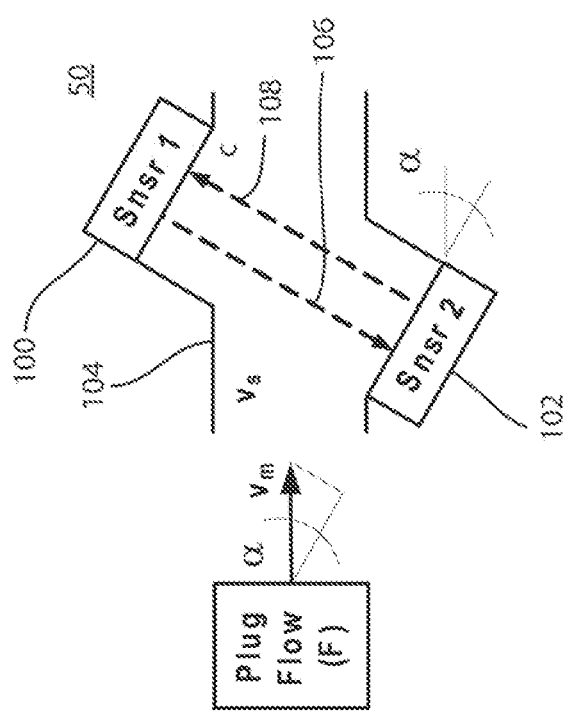
FIG. 7 depicts acoustic wave flight paths in a prior art acoustic time-of-flight flow meter configuration.

FIG. 7 depicts the typical configuration of a prior art flow meter 50, whereby the sensors 100, 102 used to measure time-of-flight t are mounted to a conduit 104 at an inclination a to the direction of flow F. A first sensor 100 transmits an acoustic wave 106 to, and receives an acoustic wave 108 from, a second sensor 102. A second sensor 102 transmits an acoustic wave 108 to, and receives an acoustic wave 106 from, a first sensor 100. Flow F is represented as a plug flow with a media speed $v_m$ dependent on the cross-section of the conduit 104 in which it travels. In this manner, flow F affects speed v as there exists a component of the media speed $v_m$ (more formally its associated velocity vector) along the direction of travel of the acoustic waves 106, 108. The affect of flow F on time-of-flight t is subtractive if the acoustic wave 108 is traveling downstream with flow F or additive if the acoustic wave 106 is traveling upstream against flow F.

FIG. 8 depicts relevant aspects of the construction of the prior art flow meter 50 in FIG. 7 for use in examination of the design parameters of interest. The symbols used to denote the various construction aspects are as shown below. For simplicity of discussion, the conduit 104 cross-section is rectangular and the walls of the conduit 104 have no thickness. The discussion that follows applies in the plane of the figure, but is understood to extend through the thickness of the conduit 104.

α is sensor mounting inclination
d is sensor diameter
t is conduit height
w is conduit width
A-H are points related to the sensor-conduit mounting As envisioned, flow F travels as a plug from a position delineated by segment AB to a position delineated by segment EF. This defines two regions where the media is considered static and speed v is unaffected by flow F, within triangle CDE and within triangle AGH. This also defines a region where the media is moving and speed v is affected by flow F, within parallelogram ACEG, since there is a component of the media speed $v_m$ (more formally its associated velocity vector) along the diagonal direction traveled by acoustic waves 106, 108. In order to properly respond to gas composition changes, the media in polygon ABCDEFGH must be fully exchanged. With this understanding, the following equations below can be shown to apply.

$$t_{12} = \frac{d \tan\alpha}{v_s} + \frac{\sqrt{w^2 + w^2\tan^2\alpha}}{v_s - v_m\sin\alpha} \quad (26)$$

$$t_{21} = \frac{d \tan\alpha}{v_s} + \frac{\sqrt{w^2 + w^2\tan^2\alpha}}{v_s + v_m\sin\alpha} \quad (27)$$

$$\Delta(t_{XY}) = t_{XY2} - t_{XY1} \quad (28)$$

$$\Delta t = t_{12} - t_{21} \quad (29)$$

$$\Delta(\Delta t) = \Delta t_2 - \Delta t_1 \quad (30)$$

$$V = tw\tan\alpha + dt\sqrt{w^2 + w^2\tan^2\alpha} + d^2 t\tan\alpha \quad (31)$$

$\Delta(t_{XY})$ is time-of-flight change in $t_{XY}$
$t_{XY2}$ is time-of-flight $t_{XY}$ for test point 2
$t_{XY1}$ is time-of-flight $t_{XY}$ for test point 1
$\Delta t$ is time-of-flight difference
$\Delta(\Delta t)$ is time-of-flight difference change
$\Delta t_2$ is time-of-flight difference for test point 2
$\Delta t_1$ is time-of-flight difference for test point 1
V is conduit volume FIG. 9 depicts the configuration of a new flow meter 60 according to the present application, whereby the sensors 70, 75 used to measure time-of-flight t are mounted to a conduit 80 without inclination to the direction of flow F, and across from an alternately flat and sloped surface 90. The surface 90 splits the acoustic waves from each sensor 70, 75. A portion of the acoustic wave 85 from a first sensor 70 is transmitted back to the first sensor 70. Another portion of the acoustic wave 86 from the first sensor 70 is transmitted to a second sensor 75. A portion of the acoustic wave 87 from a second sensor 75 is transmitted back to the second sensor 75. Another portion of the acoustic wave 88 from the second sensor 75 is transmitted to the first sensor 70. Flow F is represented as a plug flow with a media speed $v_m$ dependent on the cross-section of the conduit 80 in which it travels. In this manner, flow F affects speed v as there exists a component of the media speed $v_m$ (more formally its associated velocity vector) along the direction of travel of the acoustic waves 86, 88. The affect of flow F on time-of-flight t is subtractive if the acoustic wave 88 is traveling downstream with flow F or additive if the acoustic wave 86 is traveling upstream against flow F.

Figure 10:
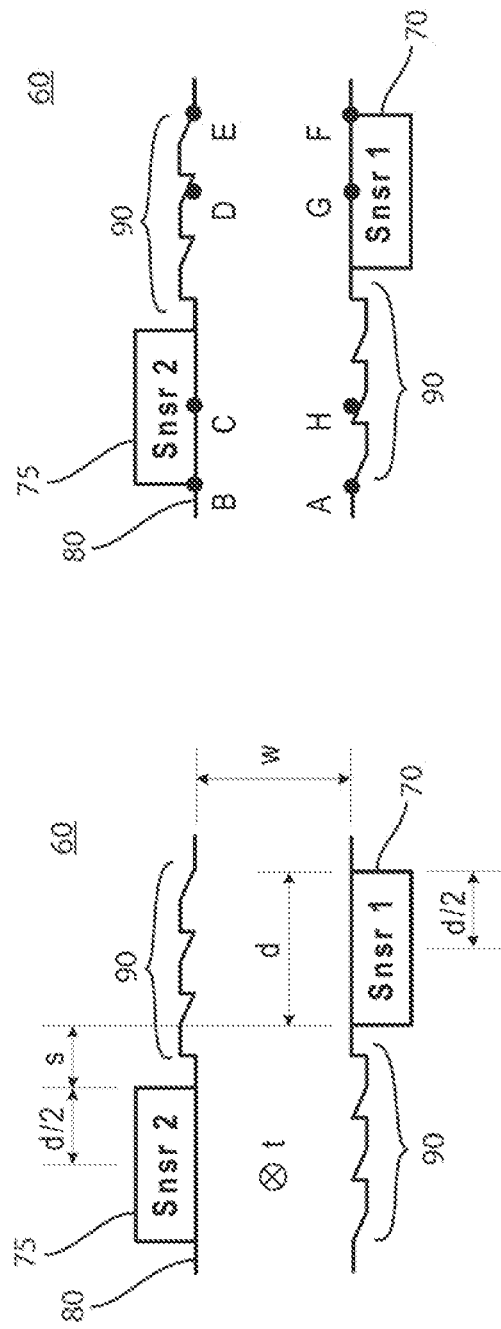
FIG. 10 depicts an embodiment of the acoustic time-of-flight flow meter for gas composition and flow according to the present application.

FIG. 10 depicts relevant aspects of the construction of the new flow meter 60 in FIG. 9 for use in examination of the design parameters of interest. The symbols used to denote the various construction aspects are as shown below. For simplicity of discussion, the conduit 80 cross-section is rectangular, the walls of the conduit 80 have no thickness, and the dimensions of the alternately flat and sloped surface 90 are ignored as they can be made negligibly small in the analysis below by appropriate choice of feature size. The discussion that follows applies in the plane of the figure, but is understood to extend through the thickness of the conduit 80.

β is acoustic wave travel inclination
d is sensor diameter
s is sensor-to-sensor spacing
t is conduit height
w is conduit width
A, B, E, F are points related to the sensor-conduit mounting
C, D, G, H are points along the conduit wall along sensor centerlines As envisioned, flow F travels as a plug from a position delineated by segment AB to a position delineated by segment EF. An acoustic wave 85, 87 from a sensor 70, 75 back to itself is unaffected by flow F, since there is no component of the media speed $v_m$ (more formally its associated velocity vector) along the direction traveled by acoustic waves 85, 87. An acoustic wave 86, 88 from a sensor 70, 75 to the other sensor 75, 70 is affected by flow F, since there is a component of the media speed $v_m$ (more formally its associated velocity vector) along the diagonal direction traveled by acoustic waves 86, 88. In order to properly respond to gas composition changes, the media in polygon ABCDEFGH must be fully exchanged. With this understanding, the following equations below can be shown to apply.

$$t_{11}, t_{22} = \frac{2w}{v_s} \quad (32)$$

$$t_{12} = \frac{2w}{v_s} + \frac{\sqrt{w^2 + (d+s)^2}}{v_s - v_m \sin\beta} \quad (33)$$

$$t_{21} = \frac{2w}{v_s} + \frac{\sqrt{w^2 + (d+s)^2}}{v_s + v_m \sin\beta} \quad (34)$$

$$\beta = \tan^{-1}\left(\frac{d+s}{w}\right) \quad (35)$$

$$V = (2d+s)tw \quad (36)$$

The advantages of the configuration of the new flow meter 60 over the configuration of the prior art flow meter 50 can be demonstrated by examination of the three design parameters for a pair of challenging test cases. In a first test case, the incremental time-of-flight difference change $\Delta(\Delta t)$ associated with a minimal change in flow F is examined. In a second test case, the incremental time-of-flight change $\Delta(t)$ associated with a minimal change in gas composition, caused by anesthetic concentration c, is examined. In both cases, anesthetic, carrier gas, and carrier gas flow have been chosen to represent a very challenging scenario from the standpoint of flow meter design. The test cases listed below are illustrative and are not intended to limit the scope of the claimed subject matter.

Test Case 1: F=150 to F=250 mL/min, in Air, T=293.15K
Test Case 2: Halothane 4.9% to 5.0%, F=150 mL/min, in 25% oxygen/75% nitrous oxide, T=293.15K The prior art flow meter 50 and the new flow meter 60 are assigned the same values for corresponding construction dimensions for fair and direct comparison (d=10 mm, t=10 mm, w=10 mm). The remaining free design parameter for the prior art flow meter 50, inclination angle α, is varied over a reasonable range. For each value of inclination angle α, the remaining free design parameter for the new flow meter 60, sensor spacing s, is allowed to vary to give first, an equal value of time-of-flight difference change $\Delta(\Delta t)$, related to flow change, as for the prior art flow meter 50, and then second, an equal value of volume V as for the prior art flow meter 50. The corresponding values of time-of-flight change $\Delta(t)$, related to anesthetic concentration c change are calculated. See the tables below for the results. Units are as follows: [F]=mL/min, $[t_{XY}]$=μs, $[\Delta t]$=ns, $[\Delta(\Delta t)]$=ns, [V]=mL, [s]=mm, [c]=% v/v, $[\Delta(t)]$=ns.

TABLE 1

Flow change test case, with α = 22.5°

| | Prior Art Configuration | | | | | New Configuration | | | | | |
| --- | --- | --- | --- | --- | --- | --- | --- | --- | --- | --- | --- |
| F | $t_{12}$ | $t_{21}$ | Δt | Δ(Δt) | V | $t_{12}$ | $t_{21}$ | Δt | Δ(Δt) | V | s |
| 150 | 43.469 | 43.468 | 1.747 | | | 89.528 | 89.527 | 1.747 | | | |
| 250 | 43.470 | 43.467 | 2.912 | 1.165 | 1.91 | 89.529 | 89.526 | 2.912 | 1.165 | 1.41 | −5.90 |
| 150 | 43.469 | 43.468 | 1.747 | | | 93.378 | 97.374 | 3.842 | | | |
| 250 | 43.470 | 43.467 | 2.912 | 1.165 | 1.91 | 97.379 | 97.373 | 6.403 | 2.561 | 1.91 | −0.89 |

TABLE 2

Anesthetic change test case, with α = 22.5° and s determined previously

| | Prior Art Configuration | | | | | New Configuration | | | |
| --- | --- | --- | --- | --- | --- | --- | --- | --- | --- |
| C | $t_{12}$ | Δ(t) | $t_{21}$ | Δ(t) | V | $t_{11}, t_{22}$ | Δ(t) | V | s |
| 4.9 | 58.563 | | 58.560 | | | 78.259 | | | |
| 5.0 | 58.659 | 95.792 | 58.655 | 95.778 | 1.91 | 78.387 | 128.003 | 1.41 | −5.90 |

TABLE 2-continued

Anesthetic change test case, with α = 22.5° and s determined previously

| | Prior Art Configuration | | | | | New Configuration | | | |
|---|---|---|---|---|---|---|---|---|---|
| C | $t_{12}$ | Δ(t) | $t_{21}$ | Δ(t) | V | $t_{11}, t_{22}$ | Δ(t) | V | s |
| 4.9 | 58.563 | | 58.560 | | | 78.259 | | | |
| 5.0 | 58.659 | 95.792 | 58.655 | 95.778 | 1.91 | 78.387 | 128.003 | 1.91 | −0.89 |

TABLE 3

Flow change test case, with α = 45.0°

| | Prior Art Configuration | | | | | New Configuration | | | | |
|---|---|---|---|---|---|---|---|---|---|---|
| F | $t_{12}$ | $t_{21}$ | Δt | Δ(Δt) | V | $t_{12}$ | $t_{21}$ | Δt | Δ(Δt) | V | s |
| 150 | 70.122 | 79.118 | 4.218 | | | 99.167 | 99.163 | 4.128 | | | |
| 250 | 70.124 | 70.117 | 7.030 | 2.812 | 3.41 | 99.169 | 99.162 | 7.030 | 2.812 | 2.00 | 0.00 |
| 150 | 70.122 | 79.118 | 4.218 | | | 133.992 | 133.982 | 10.183 | | | |
| 250 | 70.124 | 70.117 | 7.030 | 2.812 | 3.41 | 133.996 | 133.979 | 16.972 | 6.789 | 3.41 | 14.14 |

TABLE 4

Anesthetic change test case, with α = 45.0° and s determined previously

| | Prior Art Configuration | | | | | New Configuration | | | |
|---|---|---|---|---|---|---|---|---|---|
| C | $t_{12}$ | Δ(t) | $t_{21}$ | Δ(t) | V | $t_{11}, t_{22}$ | Δ(t) | V | S |
| 4.9 | 94.471 | | 94.463 | | | 78.259 | | | |
| 5.0 | 94.625 | 154.530 | 94.617 | 154.495 | 3.41 | 78.387 | 128.003 | 2.00 | 0.00 |
| 4.9 | 94.471 | | 94.463 | | | 78.259 | | | |
| 5.0 | 94.625 | 154.530 | 94.617 | 154.495 | 3.41 | 78.387 | 128.003 | 3.41 | 14.14 |

TABLE 5

Flow change test case, with α = 67.5°

| | Prior Art Configuration | | | | | New Configuration | | | | |
|---|---|---|---|---|---|---|---|---|---|---|
| F | $t_{12}$ | $t_{21}$ | Δt | Δ(Δt) | V | $t_{12}$ | $t_{21}$ | Δt | Δ(Δt) | V | s |
| 150 | 146.023 | 146.013 | 10.183 | | | 133.992 | 133.982 | 10.183 | | | |
| 250 | 146.026 | 146.009 | 16.972 | 6.789 | 7.44 | 133.986 | 133.979 | 16.972 | 6.789 | 3.41 | 14.14 |
| 150 | 146.023 | 146.013 | 10.183 | | | 247.438 | 247.410 | 25.170 | | | |
| 250 | 146.026 | 146.009 | 16.972 | 6.789 | 7.44 | 247.447 | 247.401 | 45.284 | 18.114 | 7.44 | 54.40 |

TABLE 6

Anesthetic change test case, with α = 67.5° and s determined previously

| | Prior Art Configuration | | | | | New Configuration | | | |
|---|---|---|---|---|---|---|---|---|---|
| C | $t_{12}$ | Δ(t) | $t_{21}$ | Δ(t) | V | $t_{11}, t_{22}$ | Δ(t) | V | S |
| 4.9 | 196.726 | | 196.707 | | | 78.259 | | | |
| 5.0 | 197.048 | 321.798 | 197.029 | 321.714 | 7.44 | 78.387 | 128.003 | 3.41 | 14.14 |
| 4.9 | 196.726 | | 196.707 | | | 78.259 | | | |
| 5.0 | 197.048 | 321.798 | 197.029 | 321.714 | 7.44 | 78.387 | 128.003 | 7.44 | 54.40 |

Comparison of the configurations for the prior art flow meter 50 and new flow meter 60 is readily accomplished by examination of the values in the preceding tables. With regards to time-of-flight t magnitude, all values of $t_{XX}$ and $t_{XY}$ in the tables are relatively large with respect to what can be measured with commercially available sensors and electronics, making this design parameter not of concern. With regards to time-of-flight change Δ(t) for incremental anesthetic concentration c changes, all values of Δ(t) in the tables are reasonable with respect to what can be measured with commercially available sensors and associated electronics, making this design parameter not of concern. The focus of the comparison then, is on the time-of-flight difference change $\Delta(\Delta t)$ for incremental flow F changes and on the volume V of the conduits 104, 80.

The table below summarizes the values of the time-of-flight difference change $\Delta(\Delta t)$ and volume V of the conduits 104, 80 for the incremental flow F change test cases from the preceding tables for both flow meters 50, 60 and computes the percentage difference relative to the values for the prior art flow meter 50.

TABLE 7

Summary of values related to flow change test cases

| | Prior Art Configuration | | New Configuration | | Difference (%) New Relative To Prior Art | |
|---|---|---|---|---|---|---|
| α | $\Delta(\Delta t)$ | V | $\Delta(\Delta t)$ | V | $\Delta(\Delta t)$ | V |
| 22.5 | 1.165 | 1.91 | 1.165 | 1.41 | 0.00 | −26.0 |
| 22.5 | 1.165 | 1.91 | 2.561 | 1.91 | 119.9 | 0.00 |
| 45.0 | 2.812 | 3.41 | 2.812 | 2.00 | 0.00 | −41.4 |
| 45.0 | 2.812 | 3.41 | 6.789 | 3.41 | 141.4 | 0.00 |
| 67.5 | 6.789 | 7.44 | 6.789 | 3.41 | 0.00 | −54.1 |
| 67.5 | 6.789 | 7.44 | 18.114 | 7.44 | 166.8 | 0.00 |

With regards to time-of-flight difference change $\Delta(\Delta t)$ for incremental flow F changes, all values of $\Delta(\Delta t)$ in the tables are relatively small with respect to what can be measured with commercially available sensors and electronics. Thus, any flow meter configuration that has larger values for this design parameter will have feasibility, performance, and/or cost advantages. As can be seen from the table above for incremental flow F changes, the configuration for the new flow meter 60 has a substantially larger magnitude of time-of-flight difference change $\Delta(\Delta t)$ for a given volume V, or, has a substantially smaller volume V of the conduits 104, 80 for a given time-of-flight difference change $\Delta(\Delta t)$.

Thus, as has been quantitatively shown, the configuration of the new flow meter 60 according to the present application has been shown to have feasibility, performance, and/or cost advantages over the prior art flow meter 50 in terms of the key design parameters of time-of-flight difference change $\Delta(\Delta t)$, loosely referred to as time-of-flight change magnitude in the 'Background', and flow meter volume V. In addition, by way of qualitative comparison, the configuration of the new flow meter 60 according to the present application has advantages over the prior art flow meter 50 in that it requires only a single direct time-of-flight t measurement for gas composition work, and its construction promotes less flow disturbance in the conduit 80.

Implementation of the flow meter 60 includes various embodiments. If an existing conduit does not include an alternately flat and sloped surface 90, then the flow meter 60 may be implemented as an integrated device including the first and second sensor 70, 75 as well as conduit 80 having a portion with an alternately flat and sloped surface 90. The integrated device is then placed in series with the existing conduit. When an existing conduit is already fashioned with an alternately flat and sloped surface 90, then the flow meter 60 may be implemented as a discrete device by configuring a first sensor 70 and a second sensor 75 on the walls of the existing conduit. As discussed previously, signals from the first and second sensors 70, 75 are received by a controller (not depicted).

The various embodiments of the flow meter 60 enable various embodiments of the vaporizer 10. The flow meter 60 at the inlet conduit 20 and the flow meter 60 at the outlet conduit 30 may be configured either as integrated or discrete devices inside the physical structure of the vaporizer 10), or physically upstream and downstream from the vaporizer 10. As discussed previously, signals from the first, second, third, and fourth sensors 1, 2, 3, 4 are received by a controller (not depicted).

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A flow meter for measuring gas flow in a conduit, comprising:
   a first sensor configured on a wall of the conduit;
   a first inside surface of the conduit configured across from the first sensor in a direction perpendicular to the flow, wherein the first inside surface is alternately flat and sloped such that both the flat and sloped portions are across from the first sensor and such that a first acoustic wave transmitted in the direction perpendicular to the flow by the first sensor is split by the first inside surface, wherein a first portion of the first acoustic wave is reflected off a flat portion of the first inside surface back to the first sensor;
   a second sensor configured on the wall of the conduit, and configured downstream or upstream on the conduit relative to the first sensor; and
   a second inside surface of the conduit configured across from the second sensor in the direction perpendicular to the flow, wherein the second inside surface is alternately flat and sloped such that both the flat and sloped portions are across from the second sensor and such that a second portion of the first acoustic wave reflected from a sloped portion of the first inside surface is reflected from a sloped portion of the second inside surface to the second sensor,
   wherein a second acoustic wave transmitted in the direction perpendicular to the flow by the second sensor is split by the second inside surface, wherein a first portion of the second acoustic wave is reflected off a flat portion of the second inside surface back to the second sensor, and further wherein a second portion of the second acoustic wave is reflected from the sloped portion of the second inside surface to the sloped portion of the first inside surface to the first sensor, and
   further wherein a controller computes the flow in the conduit by measuring an effect the flow has on the second portions of the first and second acoustic waves.

2. The flow meter of claim 1, wherein the first sensor and the second sensor are ultrasonic time-of-flight sensors.

3. The flow meter of claim 1, wherein the first portions of the first and second acoustic waves are not affected by the flow.

4. The flow meter of claim 1, wherein the conduit is physically located in an anesthetic vaporizer.

5. The flow meter of claim 1, wherein the conduit is physically located external in relation to an anesthetic vaporizer, and further wherein the conduit is an inlet or outlet conduit of the anesthetic vaporizer.

6. The flow meter of claim 1, wherein the first portion of the first or second acoustic wave is used to compute an anesthetic concentration of a gas in the conduit.

7. The flow meter of claim 1, wherein the controller computes the flow by measuring the effect of the flow on the time-of-flight of each of the second portions of the first and second acoustic waves.

8. The flow meter of claim 7, wherein the effect of flow on the time-of-flight of the second portions of the first or second acoustic waves is subtractive if the second portion of the acoustic wave is traveling in a downstream direction with the flow.

9. The flow meter of claim 7, wherein the effect of flow on the time-of-flight of the second portions of the first or second acoustic waves is additive if the second portion of the acoustic wave is traveling in an upstream direction with the flow.

10. A flow meter for measuring gas flow in a conduit, comprising:
a first sensor configured on a wall of the conduit;
a first inside surface of the conduit configured directly across from the first sensor in a direction perpendicular to the flow, wherein the first inside surface is alternately flat and sloped such that both the flat and sloped portions are across from the first sensor and such that a first acoustic wave transmitted in the direction perpendicular to the flow by the first sensor is split by the first inside surface, wherein a first portion of the first acoustic wave is reflected off a flat portion of the first inside surface back to the first sensor;
a second sensor configured on the wall of the conduit, and configured downstream or upstream on the conduit, and on an opposite wall, relative to the first sensor; and
a second inside surface of the conduit configured directly across from the second sensor in a direction perpendicular to the flow, wherein the second inside surface is alternately flat and sloped such that both the flat and sloped portions are across from the second sensor and such that a second portion of the first acoustic wave reflected from a sloped portion of the first inside surface is reflected from a sloped portion of the second inside surface to the second sensor,
wherein a second acoustic wave transmitted in the direction perpendicular to the flow by the second sensor is split by the second inside surface, wherein a first portion of the second acoustic wave is reflected off a flat portion of the second inside surface back to the second sensor, and further wherein a second portion of the second acoustic wave is reflected from the sloped portion of the second inside surface to the sloped portion of the first inside surface to the first sensor, and further wherein a controller computes the flow in the conduit by measuring an effect the flow has on the second portions of the first and second acoustic waves.

11. A flow meter for measuring gas flow in a conduit, comprising:
a first sensor configured on a wall of the conduit;
a first inside surface of the conduit configured across from the first sensor in a direction perpendicular to the flow, wherein the first inside surface includes a plurality of repeating, alternating flat and sloped surfaces such that both the flat and sloped portions are across from the first sensor and such that a first acoustic wave transmitted in the direction perpendicular to the flow by the first sensor is split by the first inside surface, wherein a first portion of the first acoustic wave is reflected off a flat portion of the first inside surface back to the first sensor;
a second sensor configured on the wall of the conduit, and configured downstream or upstream on the conduit relative to the first sensor; and
a second inside surface of the conduit configured across from the second sensor, wherein the second inside surface includes a plurality of repeating, alternating flat and sloped surfaces such that both the flat and sloped portions are across from the second sensor and such that a second portion of the first acoustic wave reflected from a sloped portion of the first inside surface is reflected from a sloped portion of the second inside surface to the second sensor,
wherein a second acoustic wave transmitted in the direction perpendicular to the flow by the second sensor is split by the second inside surface, wherein a first portion of the second acoustic wave is reflected off a flat portion of the second inside surface back to the second sensor, and further wherein a second portion of the second acoustic wave is reflected from the sloped portion of the second inside surface to the sloped portion of the first inside surface to the first sensor, and further wherein a controller computes the flow in the conduit by measuring an effect the flow has on the second portions of the first and second acoustic waves.

* * * * *